(12) United States Patent
Given et al.

(10) Patent No.: US 9,949,989 B2
(45) Date of Patent: Apr. 24, 2018

(54) INTRANASAL MEDICATION DELIVERY DEVICE AND METHOD OF USE THEREOF

(71) Applicants: John T. Given, Canton, OH (US); William R. Ackerman, Canton, OH (US)

(72) Inventors: John T. Given, Canton, OH (US); William R. Ackerman, Canton, OH (US)

(*) Notice: Subject to any disclaimer, the term of this patent is extended or adjusted under 35 U.S.C. 154(b) by 286 days.

(21) Appl. No.: 14/687,408

(22) Filed: Apr. 15, 2015

(65) Prior Publication Data

US 2015/0297617 A1 Oct. 22, 2015

Related U.S. Application Data

(60) Provisional application No. 61/980,348, filed on Apr. 16, 2014.

(51) Int. Cl.

| | |
|---|---|
| A61K 31/57 | (2006.01) |
| A61K 31/573 | (2006.01) |
| A61K 31/575 | (2006.01) |
| A61K 31/616 | (2006.01) |
| A61K 31/192 | (2006.01) |
| A61K 31/167 | (2006.01) |
| A61K 31/485 | (2006.01) |
| A61K 31/4468 | (2006.01) |
| A61K 31/495 | (2006.01) |
| A61M 15/08 | (2006.01) |
| A61M 16/10 | (2006.01) |
| A61K 45/06 | (2006.01) |
| A61M 31/00 | (2006.01) |
| A61B 17/24 | (2006.01) |

(52) U.S. Cl.
CPC .......... *A61K 31/616* (2013.01); *A61K 31/167* (2013.01); *A61K 31/192* (2013.01); *A61K 31/4468* (2013.01); *A61K 31/485* (2013.01); *A61K 31/495* (2013.01); *A61K 31/573* (2013.01); *A61K 45/06* (2013.01); *A61M 15/08* (2013.01); *A61M 16/104* (2013.01); *A61B 17/24* (2013.01); *A61M 31/00* (2013.01); *A61M 2210/0618* (2013.01)

(58) Field of Classification Search
None
See application file for complete search history.

(56) References Cited

U.S. PATENT DOCUMENTS 6,494,204 B1 12/2002 Ponce
8,435,261 B2 5/2013 Arcand et al.

FOREIGN PATENT DOCUMENTS

EP 0780127 A1 6/1997

OTHER PUBLICATIONS

"Aptar Pharma's Nasal Spray Device Chosen for Pain Management", http://www.aptar.com/pharma/prescription-division/news/press-release/aptar-pharma%27s-nasal-spray-device-chosen-for-pain-management (2014).
"Optinose", http://www.optinose.com/, (2015).
"LMA MADett, Endotracheal Tube Mucosal Atomization Device", http://www.lmana.com/pwpcontrol.php?pwpID=6371, (2015).
"LMA MAD Nasal, Needle-Free Intranasal Drug Delivery", http://www.lmana.com/pwpcontrol.php?pwpID=6359://,(2015).
"Nasal Drug Delivery Devices: Characteristics and Performance in a Clinical Perspective—A Review", Drug Delivery and Translational Research: An Official Journal of the Controlled Release Society, Published Online Oct. 18, 2012, pp. 42-62.

*Primary Examiner* — Michael Barker
(74) *Attorney, Agent, or Firm* — Sand & Sebolt

(57) ABSTRACT

The intranasal medication delivery device and method of use thereof includes an elongated malleable member arcuately curved or pre-formed in manner complimentary to the anterior wall of a nasal cavity. One particular embodiment provides the elongated and arcuate member to deliver medication through a lumen such that the medication is deposited in a semi-solid state adjacent the anterior aspect of the nasal cavity lateral wall and to the anterior end of the superior, middle, and inferior turbinate. Another particular embodiment provides the elongated and arcuate member to deliver medication as a suppository to a location similar to that of the previous embodiment. The method of delivering the medicine provides depositing the medicine adjacent the anterior end of one of the superior turbinate, middle turbinate, and inferior turbinate. An exemplary medication can be any one of a corticosteroid, an anti-histamine, an immune active mediator, an IgE binding medication, or a decongestant.

14 Claims, 9 Drawing Sheets

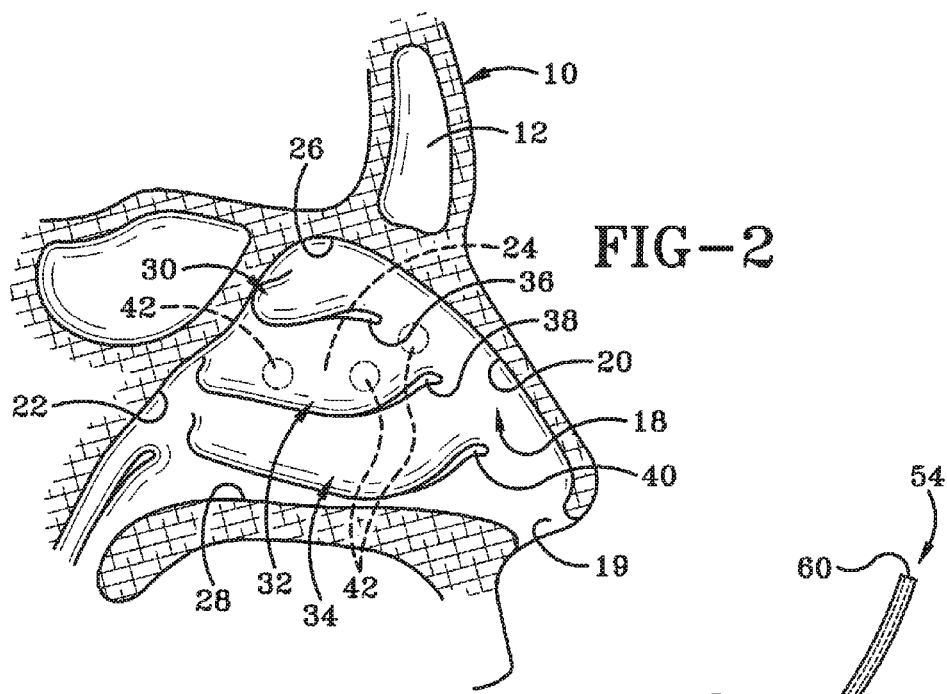
FIG-2
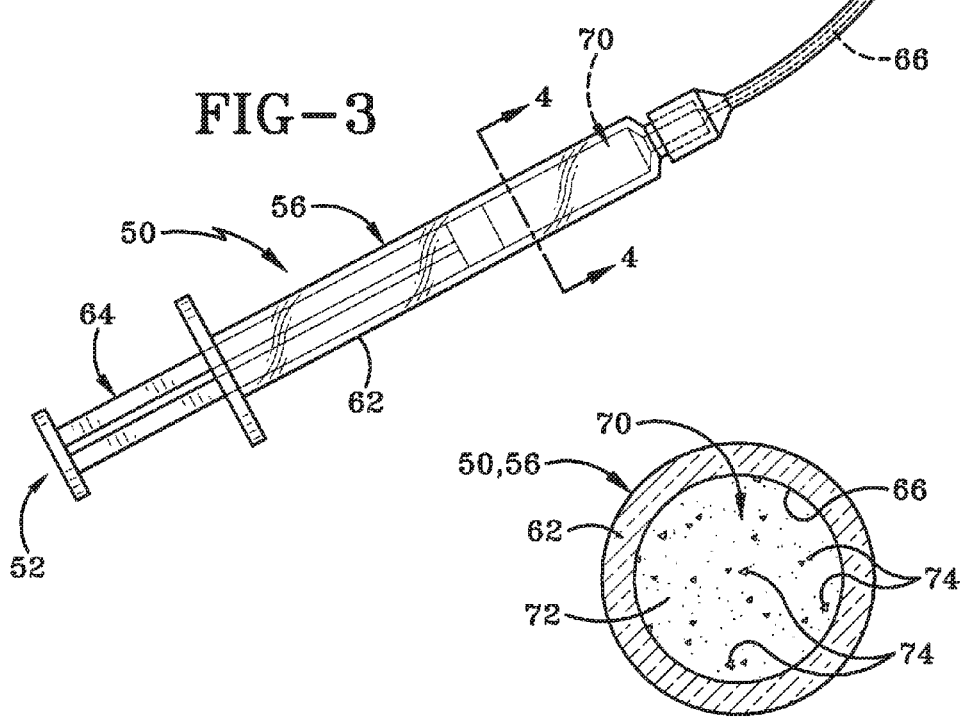
FIG-3
FIG-4

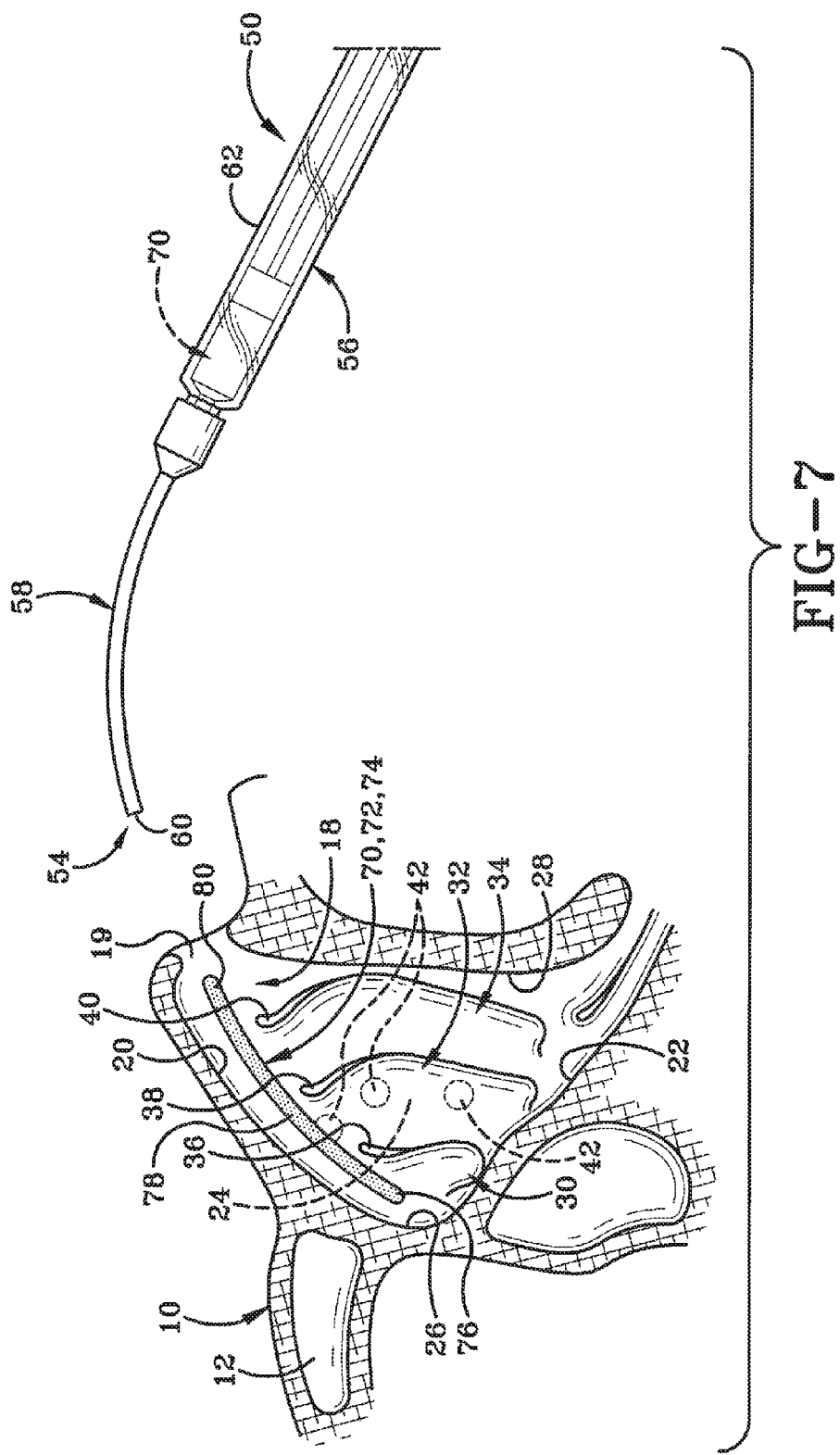

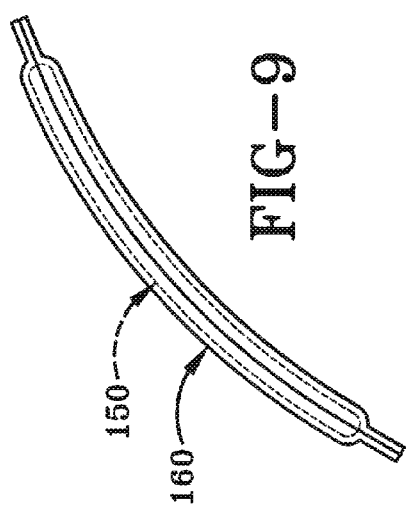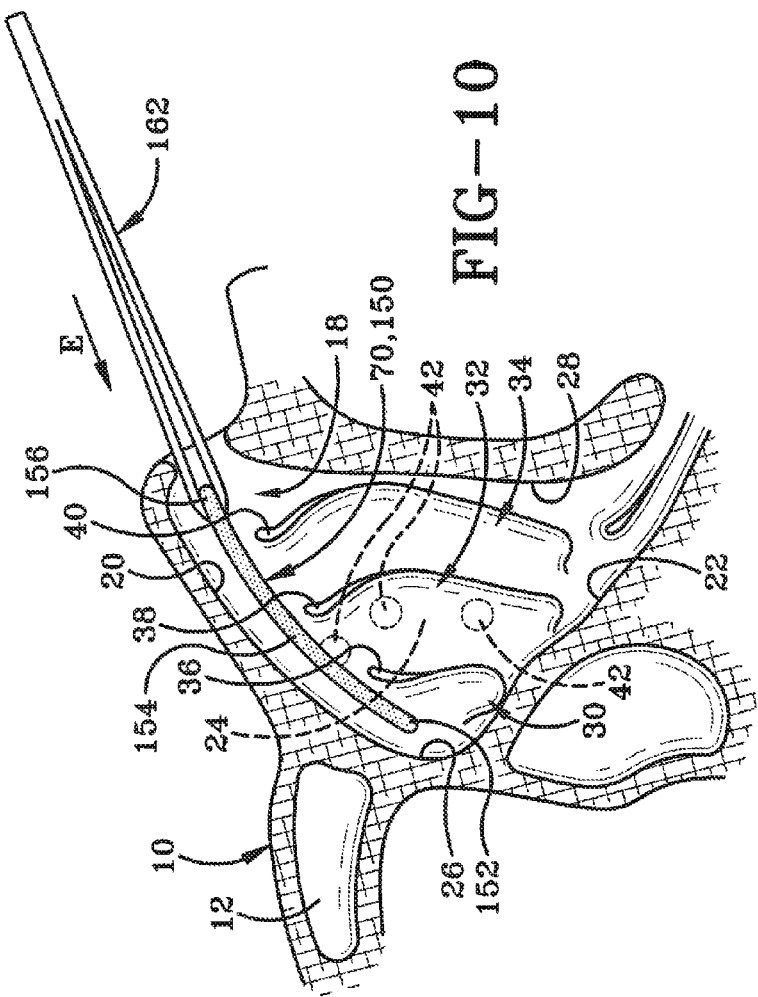

INTRANASAL MEDICATION DELIVERY DEVICE AND METHOD OF USE THEREOF

CROSS REFERENCE TO RELATED APPLICATION

This application claims the priority to and the benefit of U.S. Provisional Application Ser. No. 61/980,348 filed on Apr. 16, 2014; the entirety of which is hereby incorporated by reference as if fully rewritten herein.

BACKGROUND

Technical Field

The present invention relates generally to the field of medication delivery devices. More particularly, the present invention relates to medical devices for the delivery of intranasal cavity medication. Specifically, the present invention relates to an intranasal medication delivery device configured to deliver medication along the anterior wall and the anterior aspect of the lateral wall defining the nasal cavity.

Background

Allergies, nasal polyposis, and other inflammatory conditions of the nasal passages remain a leading cause of both acute and chronic illnesses the world over. These disorders are difficult for allergists to treat. The symptoms of these immune hypersensitivity disorders include reddening of the eyes, ocular secretions, loss of taste and smell, nasal congestion, sinusitis, ocular and palatial irritation, sneezing and mucus hypersecretion, amongst others. These symptoms occur following exposure to allergens. The allergens contact nasal tissue surfaces and irritate biological pathways. This irritation of biological pathways causes inflammation, histamine release, and immunomediators. The most common allergens are grass and/or tree pollens, hence, a nasal allergic disorders is most common during the spring and summer months. While these conditions often occur following exposure to airborne irritants, some conditions may occur without identifiable causes, such as exposure to cold temperatures free of airborne irritants.

One exemplary nasal allergic disorder is rhinoconjunctivitis. The symptoms of allergic rhinoconjunctivitis are believed to be due primarily to the stimulation of H-1 receptors by histamine, followed by reflexive activation of parasympathetic nerves causing increases in nasal secretion and obstruction. Histamine is initially released from the tissue mast cells upon sensitization of the mast cells. This sensitization results when airborne allergens combine with specific IgE antibodies attached to mast cell membranes.

SUMMARY

Issues continue to exist with nasal allergic disorders, their methods of treatment and their medication delivery devices. The present invention addresses these and other issues.

In one aspect, an embodiment may provide an intranasal medication delivery device comprising: an elongated member including a proximal section spaced apart from a distal section, the elongated member arcuately shaped in a manner complementary to a nasal cavity anterior wall; and a medication integrally formed in the elongated member including any one of a corticosteroid, an anti-histamine, an immune active mediator, an IgE binding medication, or a decongestant.

In another aspect, one embodiment may provide an intranasal medication delivery device comprising: a medication including any one of a corticosteroid, an anti-histamine, an immune active mediator, an IgE binding medication, or a decongestant; an elongated member including a proximal end and a distal end, the elongated member arcuately shaped between the proximal and distal end in a manner complementary to a nasal cavity anterior wall; and a lumen defined by the elongated member to allow the medication to move therethrough.

In another aspect, one embodiment may provide an intranasal treatment method: providing a medicine, the medicine including an any one of a corticosteroid, an anti-histamine, an immune active mediator, an IgE binding medication, or a decongestant; providing nasal tissues within the nasal cavity of a patient, the nasal tissues including a superior turbinate, a middle turbinate, and an inferior turbinate, each of the turbinate extending anteroposteriorly; and depositing the medicine adjacent the anterior end of one of the superior turbinate, middle turbinate, and inferior turbinate.

In another aspect, an embodiment may provide an intranasal medication delivery device and method thereof. The intranasal medication delivery includes an elongated member arcuately curved in manner complimentary to the anterior wall of a nasal cavity. One particular feature provides the elongated and arcuate member to deliver medication through a lumen such that the medication is deposited in a semi-solid state adjacent the anterior end of the superior, middle, and inferior turbinate. Another particular feature provides the elongated and arcuate member to deliver medication as a suppository to a location similar to that of the previous embodiment. The method of delivering the medicine provides depositing the medicine adjacent the anterior end of one of the superior turbinate, middle turbinate, and inferior turbinate. The preferred medication active ingredient is a corticosteroid.

Another aspect provides an intranasal medication delivery device comprising: an elongated member including a proximal section spaced apart from a distal section, the elongated member adapted to be disposed in an arcuate manner complementary to a nasal cavity anterior wall; and a medication integrally formed in the elongated member including at least one of a corticosteroid, an anti-histamine, an immune active mediator, an IgE binding medication, and a decongestant.

Yet another aspect provides an intranasal medication delivery device comprising: a catheter defining a lumen operatively connected to a medication container; a medication housed within the medication container, the medication including at least one of a corticosteroid, an anti-histamine, an immune active mediator, an IgE binding medication, and a decongestant, wherein the medication moves through the lumen during medication delivery; and the medication, when delivered to an anterior wall of a nasal cavity through the catheter forms an intranasal deposited elongated member including a proximal end and a distal end, the elongated member arcuately shaped between the proximal and distal end in a manner complementary to the anterior wall.

Yet another aspect provides, a method comprising the steps of:

delivering medicine in a targeted manner to a position within a nasal cavity, wherein the medicine is carried by one of the following:

(i) a semi-solid base substance within a medication container configured to be ejected through a lumen;

(ii) a self-supporting generally rigid arcuate structure curved complementary to a curvature of a nasal cavity anterior wall; and (iii) a semi-flexible linear member including a plurality of helically extending edges winding about a longitudinal axis; and wherein the medicine is delivered in a first phase state at a first viscosity, and then the medicine heats up when exposed to body temperature within the nasal cavity and transitions into a second phase state at a second viscosity lower than the first viscosity such that the medicine flows to coat at least a portion of a turbinate.

BRIEF DESCRIPTION OF THE DRAWINGS

A sample embodiment of the invention is set forth in the following description, is shown in the drawings, and is particularly and distinctly pointed out and set forth in the appended claims. The accompanying drawings, which are incorporated in and constitute a part of the specification, illustrate various examples, example methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

FIG. 2 is cross section taken along line 2-2 in FIG. 1 depicting the anatomical tissue structures contained in the nasal cavity;

FIG. 3 is a side view of a nasal medication delivery device;

FIG. 4 is a cross section taken along line 4-4 in FIG. 3 depicting a medication composition loaded into a container portion of a syringe forming a portion of the delivery device;

FIG. 7 is an operational cross section view of medication deposited within the nasal cavity after the device has been fully extracted;

FIG. 9 is a side view of an alternative embodiment of the medication delivery device;

FIG. 10 is a cross section view depicting the alternative embodiment of the device inserted into the nasal cavity;

Similar numbers refer to similar parts throughout the drawings.

DETAILED DESCRIPTION

Figure 1:
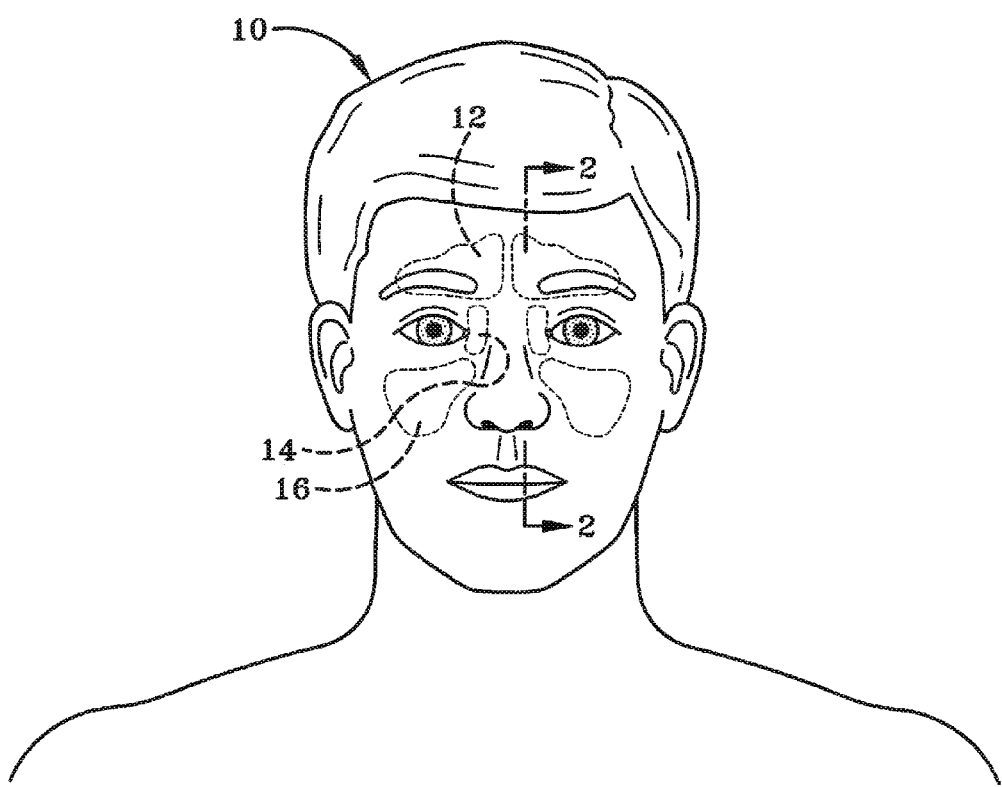
FIG. 1 is a front schematic view of anatomical tissue structures including the maxillary, ethmoid, and frontal sinuses.

As shown generally in FIG. 1 and FIG. 2 and common to human anatomy, a person 10 has four pairs of sinuses mirrored along the medial plane, namely, a pair of frontal sinuses 12, a pair of ethmoid sinuses 14, a pair of maxillary sinuses 16, and a pair of sphenoid sinuses (located more toward the back of the head than the other sinuses and not shown in FIG. 1). Normally, sinuses are filled with air, but when sinuses become blocked and filled with fluid, pathogens can grow and cause an infection. A nasal cavity 18 is a void within the head of person 10 configured to permit air to flow therethrough during the respiration process. The nasal cavity 18 shown in cross section of FIG. 2 is one of two nasal cavities contained in the face. Each left and right nasal cavity is mirroredly positioned opposite the other respective nasal cavity along the medial plane. For the purposes of this disclosure, it is to be understood that all anatomical structures referred to herein apply similarly to the opposite naval cavity. The nasal cavity 18 depicted in FIG. 2 is the left lateral nasal cavity 18.

Nasal cavity 18 is defined by an anterior wall 20 spaced apart from a posterior wall 22 defining an anteroposterior (front-to-back) direction therebetween. Nasal cavity 18 is defined by a (left) lateral wall 24 spaced apart from a medial cartilage (not shown, but lies along cross section line 2-2 in FIG. 1) defining a lateral (left-to-right) direction therebetween. Further, nasal cavity 18 is defined by a top wall 26 spaced apart from a floor wall 28 defining a vertical direction therebetween.

A superior turbinate 30, a middle turbinate 32, and an inferior turbinate 34 are positioned in nasal cavity 18. The term "turbinate" referred to herein also may medically be known as concha. Superior turbinate 30 is positioned adjacently below the top 26 and is attached to lateral wall 24. Superior turbinate 30 extends laterally inward in the medial direction from lateral wall 24 and spirals or winds about itself. Superior turbinate extends in anteroposterior direction. Middle turbinate 32 is positioned adjacent the vertical center of nasal cavity 18 beneath superior turbinate 30. Middle turbinate 32 is attached to lateral wall 24 and extends anteroposteriorly. Middle turbinate 32 extends laterally in the medial direction from lateral wall 24 and spirals or winds about itself as one having ordinarily skill in the art would understand. Inferior turbinate 34 is positioned adjacently above the floor 28 of nasal cavity 18 beneath middle turbinate 32. Inferior turbinate is attached to the lateral wall 24 and extends anteroposteriorly. Inferior turbinate 34 extends laterally in the medial direction from lateral wall and winds about itself.

A first passageway 36 is defined between the bottom side of superior turbinate 30 and the top side of the middle turbinate 32. A second passageway 38 is defined between the bottom side of middle turbinate 32 and the top side of inferior turbinate 34. A third passageway 40 is defined between the bottom side of inferior turbinate 34 and the floor 28 of nasal cavity 18. Passageways 36, 38, 40 are open and void spaces permitting air to flow therethrough.

A plurality of ostea 42 (also referred to as ostium 42), are formed in the lateral wall 24. Ostium 42 permit fluid communication of mucous flowing from the sinus cavities 12, 14, 16 into the nasal cavity 18.

With reference to FIG. 3, one embodiment of a medication delivery device is depicted generally as 50. Medication delivery device 50 comprises a proximal end 52 spaced apart from a distal end 54 defining a longitudinal direction therebetween, and comprises a medication container 56, a catheter 58 in communication with the medication container 56, and a distal exit port 60. In one particular embodiment, device 50 is an intranasal medication delivery apparatus.

Medication container 56 is defined by an annular or cylindrical sidewall 62. A plunger 64 includes two ends, a first end defining the proximal end 52 of device 50 and a second end shaped complementary to an inner annular wall of container 56. Plunger 64 is positioned within container 56 and configured to travel longitudinally in a linear manner to decrease the volume of container 56. Plunger 64 is further configured in manner similar to a conventional syringe and may include components such as gaskets, seals, and a thumb press.

Catheter 58 on device 50 is an elongated member including a proximal end and a distal end. In a particular embodiment, catheter 58 can be flexible or malleable tubing. In another particular embodiment, catheter 58 may be pre-formed at a desired curvature. Catheter 58 is coupled to annular wall 62 adjacent the proximal end and extends longitudinally towards the distal end 54. Catheter 58 formed in arcuate manner. The arcuate curve of catheter 58 is shaped complementary to the anterior wall 20 of nasal cavity 18. Catheter 58 defines a lumen 66 extending arcuately and longitudinally through the center of catheter 58. Lumen 66 extends from container 56 and terminates adjacent distal end 54 defining exit port 60. Lumen 66 is in fluid communication with medication container 56 and is configured to permit medication 70 to flow therethrough.

Medication 70 is a composition positioned within container 56 and includes an effective ingredient 72 and a base substance 74, namely by way of non-limiting example a gelling base. Effective ingredient 72 is contemplated to treat or deactivate excessive inflammation, suppress histamine production, or mediator generated symptoms. By way of non-limiting example, effective ingredient 72 can include any one of a corticosteroid, an anti-histamine, an immune active mediator, an IgE binding medication, or a decongestant. For the purposes of this disclosure, effective ingredient 72 is also referred to as corticosteroid 72. Corticosteriod 72 is a chemical that includes corticosteroid hormones synthesized in laboratories including analogues of naturally produced cortisol hormones. More specifically, in one particular embodiment corticosteroid 72 is prednisone or cortisone. Medication 70 may further comprise a small amount of mint-based oil to provide a pleasing smell to person 10. Additionally, medication 70 may include at least one of ibuprofen, naproxen, paracetamol (commercially known as acetaminophen), oxycodone/paracetamol (commercially known as Percocet or endocet), hydrocodone/paracetamol (commercially known as Lortab, Norco, or Vicodin), hydrocodone/ibuprofen (commercially known as Viocprofen), oxycodone/aspirin (commercially known as Percodan), oxycodone/naloxone (commercially known as Targin, Targiniq, and Tarinact), morphine/naltrexone (commercially known as Embeda), and fentanyl/fluanisone (Hypnorm).

In one particular embodiment, base 74 is a gelled (semi-solid) form of an anesthetic such as procaine, lidocaine, or novocaine. One exemplary non-limiting base is a prescription only lidocaine hydrochloride Jelly USP, 2%. Lidocaine HCl Jelly 2% (base 74) is a sterile, aqueous solution of lidocaine hydrochloride, hypermellose, methyl and propylparaben, sodium hydroxide and/or hydrochloric acid to adjust pH between 6.0 and 7.0. Base 74 possess a melting point in the approximate non-limiting temperature range of about 80 to about 90 degrees Fahrenheit. Once base 74 has melted, in one particular embodiment, medication 70 coats the turbinate and lateral wall of the nasal cavity 18, and then can be absorbed through the mucous membranes within nasal cavity 18 into the bloodstream.

As shown in FIG. 7, after medication 70 has been delivered to the nasal cavity (the medication delivery process described infra), medication 70 includes a first amount 76 of medication 70 deposited on and closely adjacent the top of anterior wall 20, and deposited adjacent the anterior side of top wall 26, and deposited adjacent the anterior section of lateral wall 24, and deposited adjacent anterior end of superior turbinate 30.

Medication 70 further includes a second amount 78 of medication 70 deposited on and closely adjacent the middle of anterior wall 20, and deposited below the anterior end of top wall 26, and deposited adjacent the middle anterior section of lateral wall 24, and deposited adjacent anterior end of middle turbinate 32.

Even further, medication 70 includes a third amount 80 of medication 70 deposited on and closely adjacent the bottom (towards the nostril 19) of anterior wall 20, and deposited below the anterior end of top wall 26, and deposited adjacent the lower anterior section of lateral wall 24, and deposited adjacent anterior end of inferior turbinate 34.

As shown in FIG. 9 and FIG. 10, an alternate embodiment of a medication delivery device is depicted generally as 150. Device 150 is an intranasal medicine delivery device comprising a generally rigid elongated member arcuately curved continuously and in a manner complementary to a nasal cavity anterior wall 20, a distal section 152 on the elongated member, a middle section 154 on the elongated member, a proximal section 156 on the elongated member, and a corticosteroid 72 integrally formed in the elongated member of device 150. Device 150 is shown individually stored within a tamper proof package 160 (FIG. 9).

Device 150 is a suppository. As a suppository, device 150 is configured to dissolve slowly over a set period of time when deposited within a human cavity, specifically the nasal cavity 18. The nasal suppository 150 comprises a mixture of medication 70 and other substances ordinarily in suppositories to possess a melting point in the approximate non-limiting temperature range of about 80 to about 90 degrees Fahrenheit. Once melted, in one particular embodiment, medication 70 coats the turbinate and nasal cavity surface and then can be absorbed through the mucous membranes within nasal cavity 18 into the bloodstream. Suppository 150 is a solid state at room temperature. This permits stable handling by the user for placement into the nasal cavity 18 through the nostril 19. In a particular example, suppository 150 may be directly inserted into nasal cavity 18 by the user, not a medical provider; however clearly, insertion by medical provider is contemplated and preferred.

Suppository 150 can be configured in a variety of non-limiting diameters, lengths, and curvatures to accommodate patients of different sizes and to permit choice by the user based on an assessment of nasal anatomy and medical needs of the recipient/patient.

Nasal suppository 150 can be made from a greasy base 74, such as cocoa butter, in which the active ingredient (corticosteroid 72) is dissolved; this grease will melt at body temperature. Alternatively, by way of non-limiting example nasal suppository 150 can be made from a water soluble base 74, such as polyethylene glycol, or nasal suppository 150 can be made from glycerin base 74 which comprises glycerol and gelatin.

When suppository 150 is deposited in the nasal cavity 18, distal section 152 of suppository 150, including medication 70, is deposited on and closely adjacent the top of anterior wall 20, and deposited adjacent the anterior side of top wall 26, and deposited adjacent the anterior section of lateral wall 24, and deposited adjacent anterior end of superior turbinate 30.

Middle section 154 of suppository 150, including medication 70, is deposited on and closely adjacent the middle of anterior wall 20, and deposited below the anterior end of top wall 26, and deposited adjacent the middle anterior section of lateral wall 24, and deposited adjacent anterior end of middle turbinate 32.

Proximal section 156 of suppository 150, including medication 70, is deposited on and closely adjacent the bottom (towards the nostril 19) of anterior wall 20, and deposited below the anterior end of top wall 26, and deposited adjacent the lower anterior section of lateral wall 24, and deposited adjacent anterior end of inferior turbinate 34.

Figure 11:
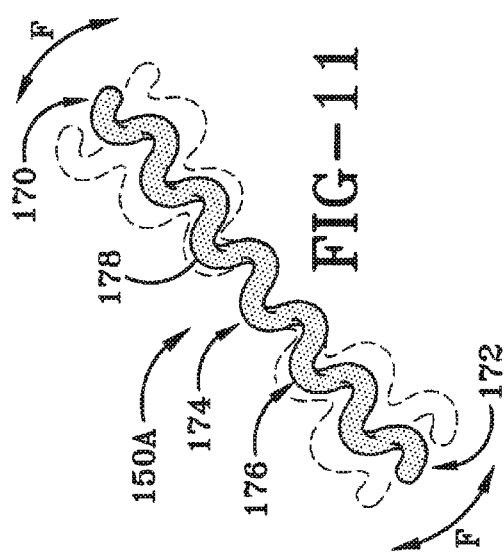
FIG. 11 is a side view of another alternative embodiment of the medication deliver device.
Figure 12:
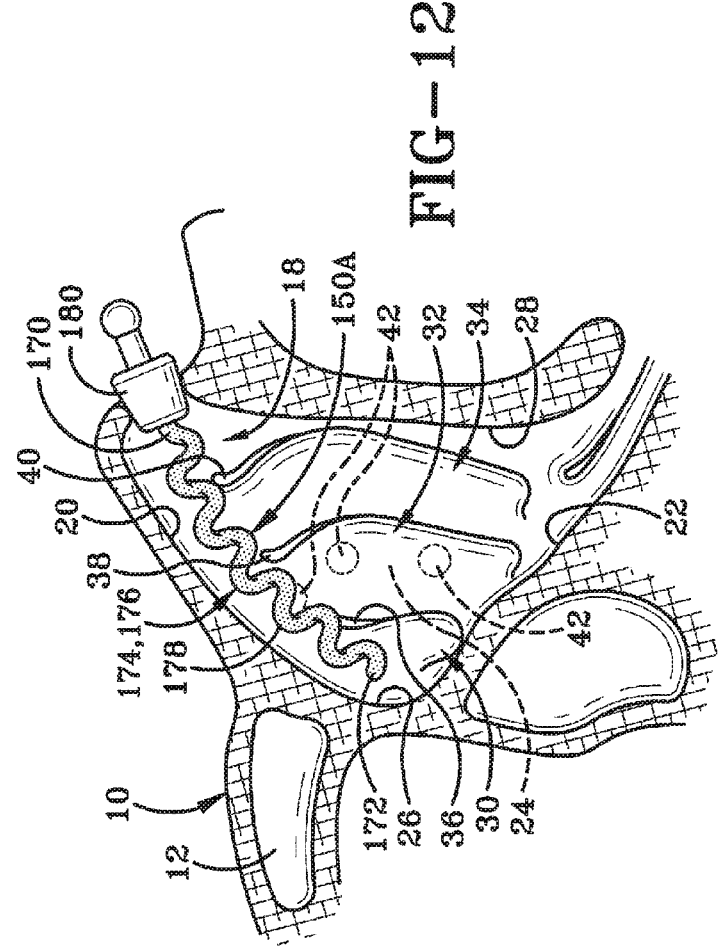
FIG. 12 is a cross section of the embodiment of FIG. 11 inserted into the nasal cavity.

As depicted in FIG. 11 and FIG. 12, device 150A is a suppository including an active ingredient of medication 70 similar to device 150. Device 150A is generally an elongated member and includes a proximal end 170 spaced apart from a distal end 172, and a middle section 174 therebetween. Device 150A further includes a semi-flexible body 176 on the device 150A extending between the proximal end 170 and the distal end 172. Device 150A is generally linear in an undelivered position outside the nasal cavity 18 (FIG. 11), and device 150A is arcuate in a delivered position inside the nasal cavity 18 (FIG. 12), wherein the semi-flexible body is configured to arcuately bend during insertion into the naval cavity.

The term generally linear with respect to device 150A refers to a straight line being able to be drawn along a longitudinal axis of 150A between proximal end 170 and distal end 172. However, as is clearly shown in FIG. 11, body 176 may helically extend and wind around the longitudinal axis between end 170 and end 172. Namely, helically extending edge 178 on the body 176 extends from adjacent the proximal end 170 to adjacent the distal end 172 spiraling or winding around the longitudinal axis forming a linear corkscrew configuration of body 176.

The diameter associated with body 176 may be uniform from proximal end 170 to distal end 172 and may be in a range from about 0.1 mm to about 15 mm, and more particularly be in a range from about 1 mm to about 10 mm. Alternatively, the body 176 may slightly taper between proximal end 170 and distal end 172 effecting a diameter at proximal end 170 greater than a diameter at distal end 172.

As depicted by the dashed-lines in FIG. 11, device 150A may flex slightly in the direction of Arrow(s) F. The flexion of device 150A permits the generally linear configuration in an undelivered position outside the nasal cavity 18 (FIG. 11), and the arcuate configuration of device 150A in a delivered position inside the nasal cavity 18 (FIG. 12). Additionally in another particular embodiment, corkscrew-like body 176 of device 150A may linearly compress and expand along the longitudinal axis of device 150A. The linear compression and expansion acts slightly similar to a spring allowing portions of device 150A to flexibly move in the longitudinal direction within the nasal cavity 18 prior to melting.

In one particular embodiment, corkscrew-like body 176 of device 150A may wind helically a number of revolution(s) about the longitudinal axis per linear inch. More particularly, device 150A may wind in a range from about 0.25 revolutions per linear inch to about 5 revolutions per linear inch. In another particular embodiment, device 150A may wind 1 revolution per linear inch.

Device 150A may further include a plug carried 180 by the device 150A adjacent the proximal end 152, wherein the plug shaped to nest within nostril 19 via an interference fit. Plug 180 may have a frustoconical configuration including tapered sidewalls. Plug 180 may have a first diameter positioned within the nasal cavity 18 past the nostril 19 and a second diameter outside the nasal cavity and in front of the nostril 19 wherein the second diameter is larger than the first diameter such that the nostril 19 engages the sidewall of plug 180 via an interference fit. Plug 180 may be formed of any suitable medically safe material, such as rubber, latex, cotton, or the like, to effectively block the nostril allowing heat to build and increase within the nasal cavity. Alternatively, plug 180 may be formed from a cotton ball connected to device 150A. Additionally, while plug 180 is shown attached to device 150A, clearly, plug 180 could be attached to device 150 as well.

As depicted in FIG. 12, when suppository 150A is deposited in the nasal cavity 18, distal end 172 of suppository 150A, including medication 70, is deposited on and closely adjacent the top of anterior wall 20, and deposited adjacent the anterior side of top wall 26, and deposited adjacent the anterior section of lateral wall 24, and deposited adjacent anterior end of superior turbinate 30.

Middle section 174 of suppository 150A, including medication 70, is deposited on and closely adjacent the middle of anterior wall 20, and deposited below the anterior end of top wall 26, and deposited adjacent the middle anterior section of lateral wall 24, and deposited adjacent anterior end of middle turbinate 32.

Proximal end 170 of suppository 150A, including medication 70, is deposited on and closely adjacent the bottom (towards the nostril 19) of anterior wall 20, and deposited below the anterior end of top wall 26, and deposited adjacent the lower anterior section of lateral wall 24, and deposited adjacent anterior end of inferior turbinate 34.

In accordance with an aspect of one embodiment, device 50, 150, or 150A allows for precise delivery of medication within the nasal cavity. The device allows an operator (i.e., a doctor) to precisely apply medicine to the anterior ends of the superior, middle, and inferior turbinate. While a patient is in the supine position, medicine 70 melts or otherwise liquefies to coat the turbinate and the edges of the ostium 42. In one particular embodiment, device 50, 150, or 150A improves the ability of the purposefully deliver medication to a targeted or deliberate area (i.e., a starting point) such that the medication 70 traverses the anteroposterior length of the turbinate by coating a majority of the surface, rather than conventional sprays which merely mist a bottom and partial region of the nasal cavity and are more affected by gravity due to the lower (i.e., less than) viscosity of a liquid than a semi-solid. This feature is a significant non-limiting advantage medication delivery device 50, 150, or 150A over conventional nasal sprays, or even saline flushes.

In accordance with another aspect of the present medication delivery device is that device 50, 150, or 150A provides medication 70 to the systemic circulation of the body. This provides a comprehensive coating of a medicated mixture 70 in a manner other than a conventional nasal spray, which only delivers medication adjacent the nostril 19. The delivery of medication 70 is along the entire vertical length of the anterior wall 20, and the anterior end of the lateral wall 24, to treat a condition of the nasal turbinate 30, 32, and 34.

In accordance with another aspect of an embodiment of the medication deliver device is that device 50, 150, or 150A may reduce pain and bleeding ordinarily associated with nasal instrumentation or nasal cavity device insertion. Further, device 50, 150, or 150A provides a controlled administration of medication 70 selectively to each of the turbinate 30, 32, and 34.

In operation, intranasal delivery device 50, 150, or 150A is configured to be inserted into the nasal cavity 18 through a nostril 19. Further in one particular embodiment, device 50, 150, 150A is inserted into the nasal cavity with the patient in the supine position.

Figure 5:
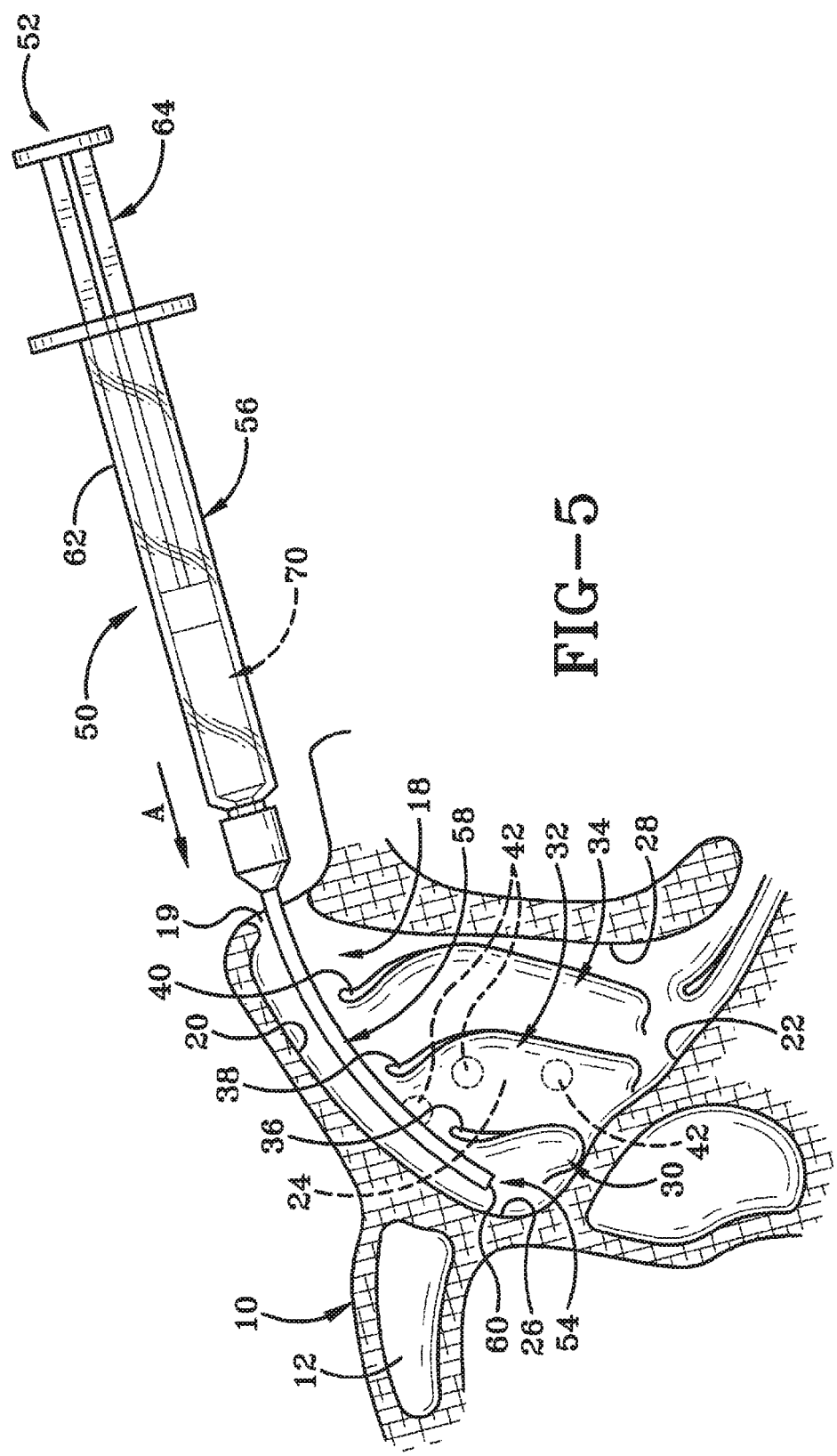
FIG. 5 is an operational cross section view of the nasal medication delivery device in an inserted position in the nasal cavity.

As shown in FIG. 5, a cross section of a supine patient details the distal end 54 breaching nostril 19 and moving into the nasal cavity 18 along and following the curvature of anterior wall 20 in the direction of Arrow A. Distal end 54 first passes inferior turbinate 34 between turbinate's 34 anterior end and the anterior wall 20 of the nasal cavity 18. Distal end 54 continues moving in the direction of arrow A following the curvature of anterior wall 20 and passes the middle turbinate 32 between turbinate's 32 anterior end and the anterior wall 20 of nasal cavity 18. Distal end 54 continues moving in the direction of arrow A following the curvature of anterior wall 20 and passes the superior turbinate 30 between turbinate's 30 anterior end and the anterior wall 20 of nasal cavity 18.

Distal end 54 comes to rest adjacent the top of anterior wall 20, adjacent the anterior end of top wall 26, adjacent the anterior section of lateral wall 24, and adjacent the anterior end of superior turbinate 30. This is considered the inserted position. When in the inserted position, the catheter body 58 is positioned adjacent the anterior wall 20 of nasal cavity in an arcuate manner complementary to that of anterior wall 20. With continued reference to the inserted position, the distal end 54 is adjacent the superior turbinate 30, a middle section of catheter 58 is adjacent the middle turbinate 32, and a proximal section of catheter 58 is adjacent the inferior turbinate 34.

Figure 6:
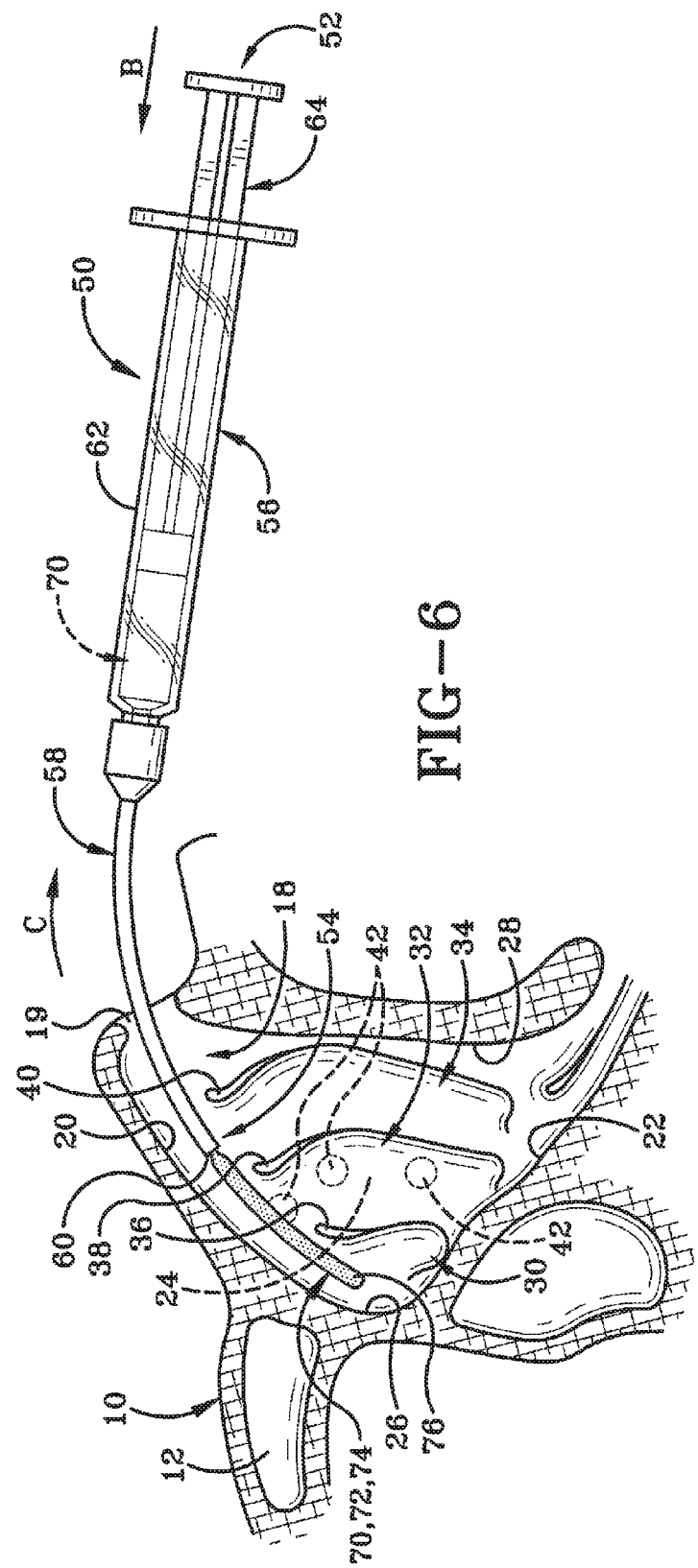
FIG. 6 is an operational cross section view of the nasal medication delivery device simultaneously depositing medication into the nasal cavity as the device is drawn outward from the nasal cavity.

As depicted in FIG. 6, a medication delivery process occurs simultaneously with the device 50 extraction process. In one particular embodiment, a medical provider simultaneously performs the medication delivery process and the device extraction process. With reference to FIG. 5 through FIG. 7, once the device 50 is considered to be in the inserted position (FIG. 5), device 50 is then ready to be extracted and deliver the medication (FIG. 6 and FIG. 7).

The medical provider stabilizes medication container 56. By way of non-limiting example container 56 may be stabilized by securing container 56 between two fingers of the medical provider. Plunger 64 is then moved in the direction of Arrow B. Arrow B is generally in the direction of towards the patients face. In one particular embodiment, plunger 64 is moved by the thumb of the medical provider. By moving plunger 64 in the direction of Arrow B, plunger contacts medication 70 stored within container 56. As movement of plunger 64 continues, medication 70 moves from container 56 through lumen 66 and eventually exits out through distal exit port 60. Medication 70 moves generally in the longitudinal direction. Once exiting port 60, a first portion of deposited medicine 70 is adjacent the top of anterior wall 20, adjacent the anterior end of top wall 26, adjacent the anterior section of lateral wall 24, and adjacent anterior end of superior turbinate 30. In this particular non-limiting embodiment, the gelled medication 70 is a non-Newtonian fluid and the gel consistency of medication 70 permits it to stay in that position a short period of time prior to liquefying (the step of liquefying described infra).

Device 50 is extracted from nasal cavity 18 through nostril 19 in the direction of Arrow C. During this extraction movement, medical provider continues to move plunger 64 in the direction of Arrow B. This causes medication 70 to be deposited in a targeted manner adjacent the anterior end of turbinate 32, 34 as device 50 is drawn or extracted outwardly from the nasal cavity 18.

As shown in FIG. 7, once device 50 has been completely extracted, medication 70 is considered to be deposited in a targeted starting area of the nasal cavity 18. In this targeted deposition position, the first amount 76 of medication 70 is adjacent the anterior end of superior turbinate 30 and adjacent the anterior aspect of lateral wall 24. The second amount 78 of medication 70 is adjacent the anterior end of middle turbinate 32 and the anterior aspect of lateral wall 24. The third amount 80 of medication 70 is adjacent the anterior end of inferior turbinate 34 and the anterior aspect of lateral wall 24. Further, in this deposited position, medication 70 is in a first phase state at a first viscosity. The first phase state of medication 70 may be a solid (i.e., suppository 150, or 150A) or a semi-solid (gel delivered by device 50). It is noteworthy that unlike known nasal-sprays, in one particular embodiment, the medication delivery device 50, 150, and 150A is preferably not in liquid form at the delivery stage (like a nasal spray), although it could be. It is only once the medication 70 has been precisely delivered in its solid or semi-solid state will it then turn to liquid.

After device 50 (or 150, 150A) has delivered the targeted deposition of medication 70, the nostril 19 of the patient is plugged with a cotton ball (or plug 180) or some other equivalent gauze. The plugging of nostril 19 causes heat to build up within the nasal cavity. Increasing the temperature in this manner assists in speeding up the liquefying process of medication 70 from its first solid or semi-solid state to the second liquid state.

Figure 8A:
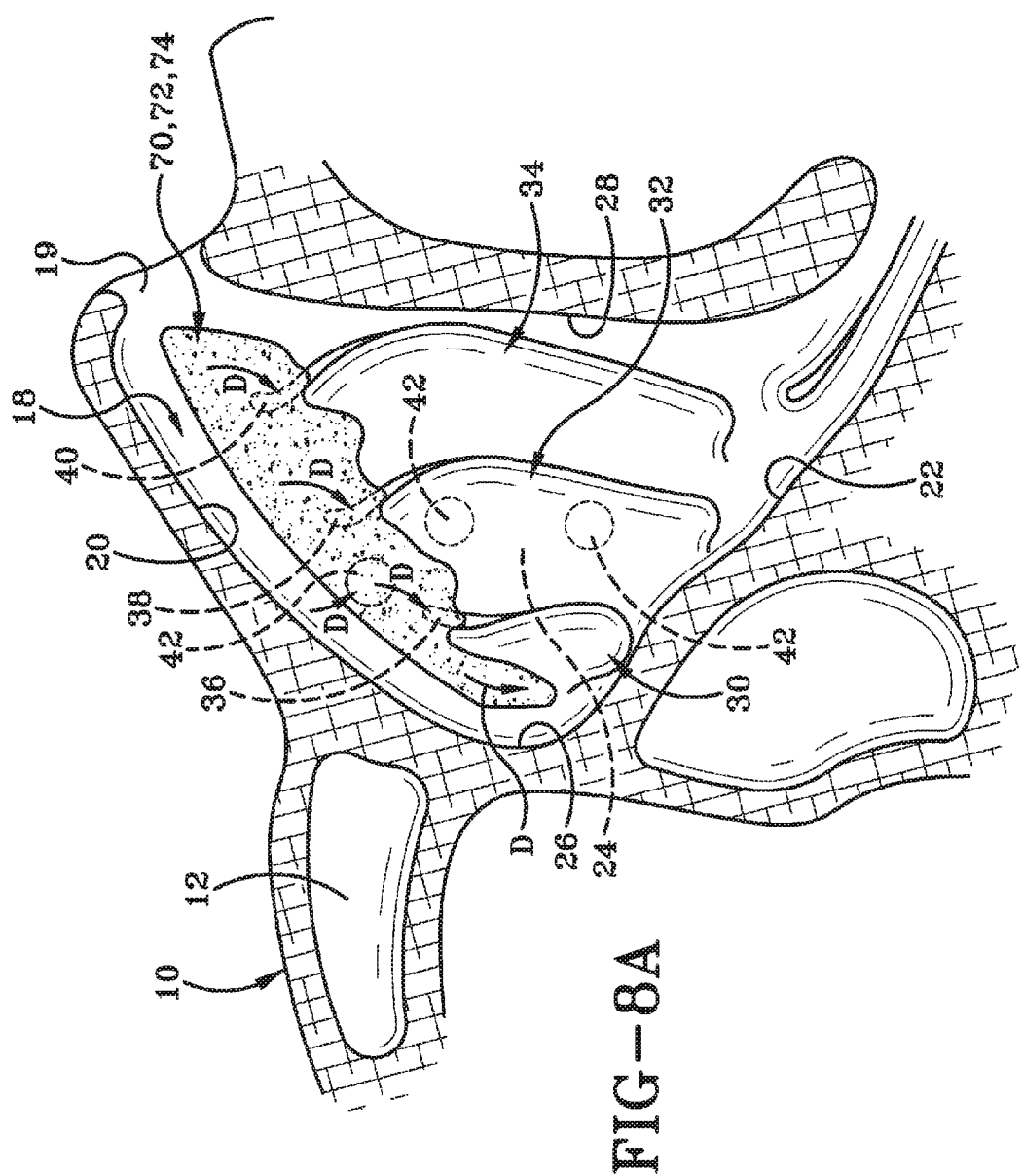
FIG. 8A is an operational cross section view of medication beginning to liquefy and coating a turbinate in the nasal cavity.
Figure 8B:
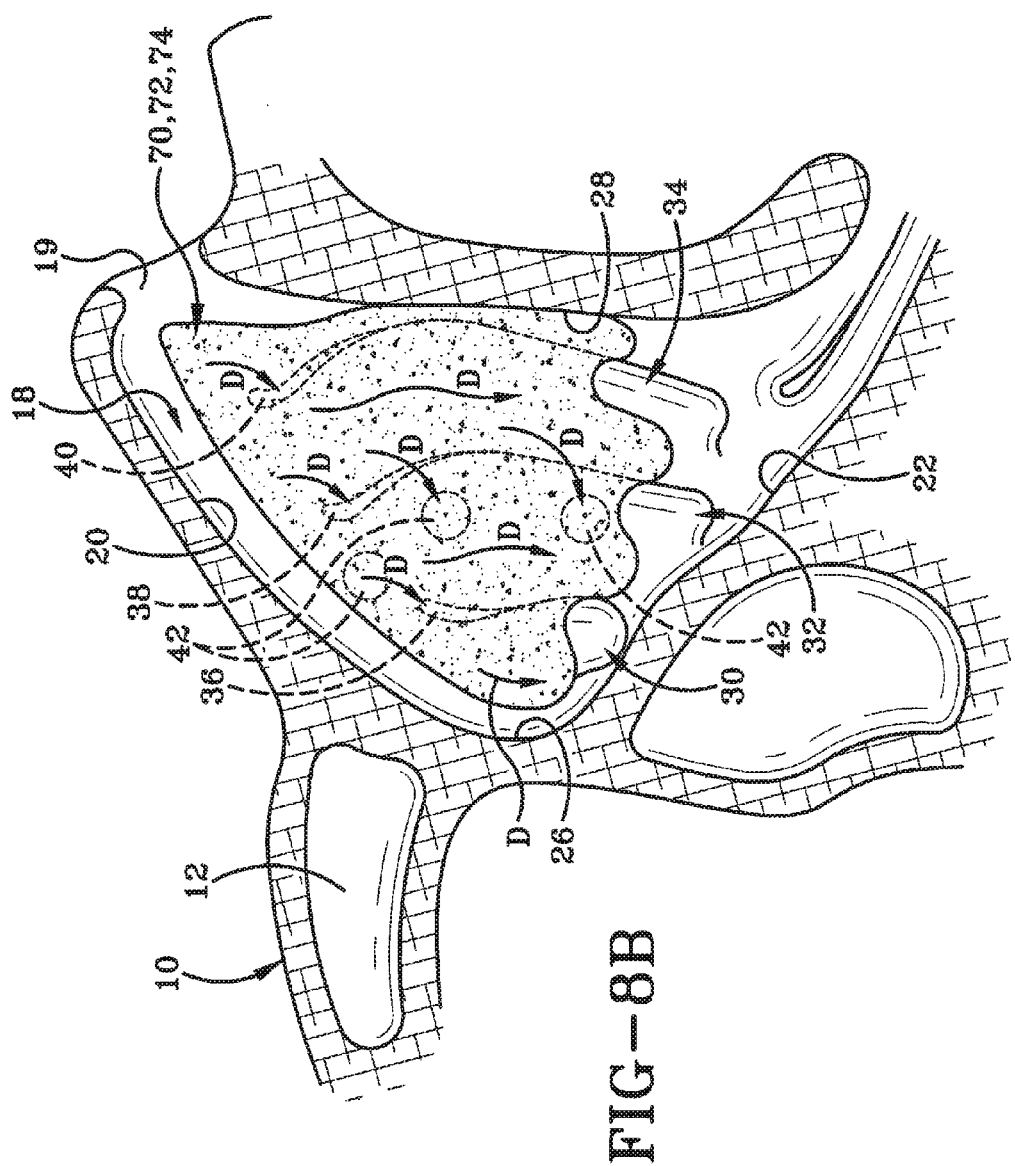
FIG. 8B is an operational cross section view of liquefied medication coating the turbinate and flowing towards ostea in the nasal cavity.

With reference to the operation depicted in FIG. 8A and FIG. 8B, medication 70 liquefies or melts at a transition temperature (i.e., a melting point). Normally, when exposed to normal body temperature, the transition temperature will be around 98° F. However, device 50, 150, or 150A may be configured to liquefy at other temperatures, such as any transition temperature between 85° F. and 110° F. The melting causes medication 70 to transition from a first phase state (solid; or semi-solid) to a second phase state (generally liquid), wherein the second phase state has a viscosity lower (i.e., less than) than that of the first phase state. Medication 70 begins to flow posteriorly (downward when the patient is in the supine position). Medication 70 moves or flows in a liquid state or semi-solid state having a lower second viscosity in the direction of Arrow D. Medication 70 flows via gravity (in the direction of Arrow(s) D) through each of the first passageway 36, the second passageway 38, and third passageway 40. As depicted in FIG. 8B, medication 70 also moves over each of the superior, middle, and inferior turbinate 30, 32, 34, respectively, to coat each turbinate. Medication flows into and through ostium 42. In one embodiment, medication 70 deposited from device 50 is a non-Newtonian fluid at the step of depositing the medicine. Then, medication 70 transitions from a non-Newtonian fluid to a Newtonian fluid adjacent the anterior end of one of the first, second, and third passageways.

When medication 70 has melted and is in the liquid state or lower viscosity state, the active ingredients, namely corticosteroid 72, may be absorbed into the blood stream. Alternatively, corticosteroid may topically treat the turbinate 30, 32, 34 and ostium 42 locally. Additional active ingredients (i.e., pain reducers) may also be absorbed by the body as well.

In operation and with reference to FIG. 9 and FIG. 10, suppository medication delivery device 150 is unwrapped from its individually sealed package 160. Once unwrapped, device 150 is inserted through nostril 19 and moving into the nasal cavity 18 in the direction of Arrow E following the curvature of anterior wall 20. In FIG. 10, device 150 is shown by way of non-limiting example being inserted utilizing a forceps 162, however clearly manual insertion is entirely possible. Distal end 152 (also referred to as distal section 152) of suppository 150 first passes inferior turbinate 34 between turbinate's 34 anterior end and the anterior wall 20 of the nasal cavity 18. Distal end 152 of suppository 150 continues moving in the direction of arrow E following the curvature of anterior wall 20 and passes the middle turbinate 32 between turbinate's 32 anterior end and the anterior wall 20 of nasal cavity 18. Distal end 152 of suppository continues moving in the direction of Arrow E following the curvature of anterior wall 20 and passes the superior turbinate 30 between turbinate's 30 anterior end and the anterior wall 20 of nasal cavity 18.

Once nasal suppository is in the inserted position (FIG. 10), the distal section 152 is positioned closely adjacent the anterior end of superior turbinate 30, the middle section 154 is positioned closely adjacent the anterior end of middle turbinate 32, and the proximal section 156 is positioned closely adjacent anterior end of inferior turbinate 34. Suppository 150 then begins to liquefy or melt in a similar manner as medicine 70 delivered by device 50 detailed above.

In operation and with reference to FIG. 12, suppository medication delivery device 150A is unwrapped or removed from a packaging. Device 150A may be individually packaged, similar to device 150 in packaging 160, or alternatively it may provided in bulk packaging. Once unwrapped, device 150A is inserted through nostril 19 in a linear form and is moved into the nasal cavity 18. Device 150A flexes in the direction of Arrow F and follows the curvature of anterior wall 20. Distal end 172 of suppository device 150A first passes inferior turbinate 34 between turbinate's 34 anterior end and the anterior wall 20 of the nasal cavity 18. Distal end 172 of suppository device 150A continues moving deeper into the nasal cavity following the curvature of anterior wall 20 and passes the middle turbinate 32 between turbinate's 32 anterior end and the anterior wall 20 of nasal cavity 18. Distal end 172 of suppository device 150A continues moving deeper into the nasal cavity following the curvature of anterior wall 20 and passes the superior turbinate 30 between turbinate's 30 anterior end and the anterior wall 20 of nasal cavity 18.

Once nasal suppository 150A is in the inserted position (FIG. 12), the distal end 172 is positioned closely adjacent the anterior end of superior turbinate 30, the middle section 174 is positioned closely adjacent the anterior end of middle turbinate 32, and the proximal end 170 is positioned closely adjacent anterior end of inferior turbinate 34. Plug 180 fits within nostril 19 sealing heat within nasal cavity 18. As heat begins to rise, suppository 150A then begins to liquefy or melt in a similar manner as medicine 70 delivered by device 50 or device 150 detailed above and flows as depicted in FIG. 8A and FIG. 8B.

Further, with respect to the insertion of device 150A, helically winding body 176 may rotate about its longitudinal axis during the insertion. The number of revolutions of body 176 dictate the number of times device 150A revolves within the nasal cavity as device 150A moves deeper into the nasal cavity.

In operation and with primary reference to the making of medication 70, a first amount of corticosteroid 72 is obtained. In this particular non-limiting example, reference is made to corticosteroid 72 as prednisone. Prednisone exhibits anti-inflammatory and immunosuppressant properties when it is converted to prednisolone in the liver. Prednisone 72 is available by prescription and ordinarily comes in 1 mg, 2.5 mg, 5 mg, and 20 mg tablets.

For an average adult, the medication deliver process described above ordinarily utilizes 40 mg of prednisone 72. Two 20 mg tablets of prednisone 72 are pulverized in a mixing dish. The pulverized prednisone 72 is then mixed with gelling base 74 to form the composition of medication 70. The amount of base 74 is usually in the amount of about 1 to 2 cc/ml, preferably about 1.5 cc/ml. The composition medication 70 is then moved into container 56 so it may be administered to the patient.

In addition to one or more of corticosteroid 72, an antihistamine, an immune active mediator, an IgE binding medication, and a decongestant, medication 70 may also be fabricated with an effective amount of peppermint oil, or similar substitute to homeopathically alleviate nasal symptoms. Medication 70 may also be fabricated with an effective amount of pain-reducing formula. Some exemplary pain reducers are oxycodone/paracetamol, hydrocodone/paracetamol, hydrocodone/ibuprofen, oxycodone/aspirin, oxycodone/naloxone, morphine/naltrexone, and fentanyl/fluanisone.

An alternatively contemplated nonlimiting example may permit device 50, 150 or 150A to selectively administer medication to an anterior end of any one or two selected turbinate. In one particular embodiment, there may be an instance where it is not desirable to deliver medication all the way to the anterior end of the superior turbinate 30. Thus, device 50, 150 or 150A can be inserted into the nasal cavity 18 to administer medication to only the middle and inferior turbinate 32, 34, respectively. Or alternatively, medication 70 could be delivered only to the anterior end of inferior turbinate 32. Or alternatively, medication 70 could be delivered only to the anterior end of the superior turbinate 30 if the case desired.

In the foregoing description, certain terms have been used for brevity, clearness, and understanding. No unnecessary limitations are to be implied therefrom beyond the requirement of the prior art because such terms are used for descriptive purposes and are intended to be broadly construed.

What is claimed:

1. An intranasal treatment method for nasal tissues within a nasal cavity of a patient, the nasal tissues including a superior turbinate, a middle turbinate, and an inferior turbinate, each turbinate extending anteroposteriorly, comprising the steps of:
providing a medicine, the medicine including an amount of a corticosteroid;
depositing the medicine adjacent one of the superior turbinate, middle turbinate, and inferior turbinate;
depositing a first portion of medicine adjacent the superior turbinate;
depositing a second portion of medicine adjacent the middle turbinate; and
depositing a third portion medicine adjacent the inferior turbinate; and
depositing the medicine in a first phase state having a first viscosity, wherein the medicine heats up within the nasal cavity and transitions into a second phase state having a second viscosity, wherein second viscosity is lower than the first viscosity.

2. The method of claim 1, wherein the first portion of medicine is deposited in a targeted manner adjacent an anterior end of the superior turbinate;
wherein the second portion of medicine is deposited in a targeted manner adjacent an anterior end of the middle turbinate; and
wherein the third portion of medicine is deposited in a targeted manner adjacent an anterior end of the inferior turbinate.

3. The method of claim 1, further comprising the step of:
effecting the transition of the medicine from the first phase state to the second phase state, such that the medicine flows to coat one of the superior, middle, and inferior turbinate.

4. The method of claim 3, wherein the transition of the medicine from the first phase state to the second phase state is accomplished by melting, wherein the medicine has a melting point of about 90° F. to about 100° F.

5. The method of claim 3, wherein the medicine is displaced via gravity from a first position adjacent an anterior aspect of a lateral wall defining a portion of the nasal cavity to a second position adjacent a nasal ostea posterior to the first position.

6. The method of claim 3, wherein the medicine is a non-Newtonian fluid at the first phase state and wherein the medicine is a Newtonian fluid at the second phase state.

7. The method of claim 3, prior to the step of depositing the medicine, further comprising the steps of:
inserting the medicine carried by a delivery device into the nasal cavity, a portion of the delivery device having an arcuate configuration complementary to a nasal cavity anterior wall; and
ejecting the medicine from the delivery device.

8. The method of claim 7, wherein the delivery device includes a proximal end and a distal end, and defines a lumen, and wherein prior to the step of depositing the medicine further comprises the steps of:
inserting the distal end of the delivery device through a nostril until the distal end of the delivery device is adjacent an anterior end of the superior turbinate; and
drawing the delivery device outward from the nasal cavity through the nostril while simultaneously ejecting the medicine through the lumen.

9. The method of claim 3, prior to the step of depositing the medicine, further comprising the steps of:
inserting the medicine through a nostril, the medicine integrally formed in a self-supporting generally rigid member.

10. The method of claim 9, wherein the self-supporting generally rigid member has an arcuate configuration curved complementary to a curvature of a nasal cavity anterior wall.

11. The method of claim 3, prior to the step of depositing the medicine, further comprising the step of:
inserting the medicine through a nostril, the medicine integrally formed in a flexible linear suppository; and
bending the flexible linear suppository, wherein the suppository is linear in an undelivered position outside the nasal cavity, and the suppository is arcuate in a delivered position inside the nasal cavity.

12. The method of claim 11, wherein the step of inserting a flexible linear suppository into the nasal cavity is accomplished by rotating the suppository, wherein the suppository includes a plurality of helically extending edges winding about a longitudinal axis of the suppository.

13. An intranasal treatment method for nasal tissues within a nasal cavity of a patient, the nasal tissues including a superior turbinate, a middle turbinate, and an inferior turbinate, each turbinate extending anteroposteriorly, comprising the steps of:
providing a medicine, the medicine including an amount of a corticosteroid;
depositing the medicine adjacent one of the superior turbinate, middle turbinate, and inferior turbinate, wherein the superior and middle turbinate define a first passageway therebetween, the middle and inferior turbinate define a second passageway therebetween, and the inferior turbinate and a floor of the nasal cavity define a third passageway therebetween;
depositing the medicine adjacent one of the first, second, and third passageways;
depositing a first portion of the medicine adjacent the first passageway;
depositing a second portion of the medicine adjacent the second passageway;
depositing a third portion of the medicine adjacent the third passageway;
wherein the first portion of medicine is deposited in a targeted manner adjacent an anterior end of the first passageway;
wherein the second portion of medicine is deposited in a targeted manner adjacent an anterior end of the second passageway;
wherein the third portion of medicine is deposited in a targeted manner adjacent an anterior end of the third passageway;
depositing a bead of medicine in a first phase state at a first viscosity wherein the bead of medicine heats up within nasal cavity and transitions into a second phase state at a second viscosity such that the medicine moves along one of the first, second, and third passageways; and
wherein the second viscosity is lower than the first viscosity.

14. An intranasal treatment method for nasal tissues within a nasal cavity of a patient, the nasal tissues including a superior turbinate, a middle turbinate, and an inferior turbinate, each turbinate extending anteroposteriorly, comprising the steps of:
providing a medicine, the medicine including an amount of a corticosteroid;
depositing the medicine adjacent one of the superior turbinate, middle turbinate, and inferior turbinate, wherein the medicine is in one of (i) a semi-solid state and (ii) a solid state, further comprising the step of:
moving the patient to a supine position, wherein the medicine heats up within nasal cavity and melts from either (i) the semi-solid state and (ii) the solid state into a liquid and the medicine flows posteriorly under gravitation force.

* * * * *